United States Patent [19]

Hennig et al.

[11] 4,154,226

[45] May 15, 1979

[54] MAGNETICALLY OPERATED CLOSURE FOR AN INTESTINAL ORIFICE

[75] Inventors: Gerhard Hennig, Gauting; Günter Willital, Hemhofen, both of Fed. Rep. of Germany

[73] Assignee: Coloplast International A/S, Espergaerde, Denmark

[21] Appl. No.: 801,326

[22] Filed: May 27, 1977

[30] Foreign Application Priority Data

Apr. 20, 1977 [DE] Fed. Rep. of Germany ....... 2717607

[51] Int. Cl.² .......................................... A61B 19/00
[52] U.S. Cl. ................................. 128/1 R; 128/283; 128/DIG. 25; 3/1
[58] Field of Search ................ 128/1 R, 283, 1.3, 1.4, 128/DIG. 25; 3/1

[56] References Cited

U.S. PATENT DOCUMENTS

| | | | |
|---|---|---|---|
| 2,243,529 | 5/1941 | Grossman et al. | 128/1 R |
| 3,565,073 | 2/1971 | Giesy | 128/283 |
| 3,939,821 | 2/1976 | Roth | 128/1 R |
| 3,952,726 | 4/1976 | Hennig et al. | 128/1 R |
| 3,958,556 | 5/1976 | Schenk | 128/1 R |

FOREIGN PATENT DOCUMENTS 2363563  6/1975  Fed. Rep. of Germany ........... 128/283

Primary Examiner—Dalton L. Truluck
Attorney, Agent, or Firm—Flynn & Frishauf

[57] ABSTRACT

An implantate comprising an essentially annular permanent magnet which is axially magnetized is located in the vicinity of an orifice from an intestine, surrounding the intestine. A plug element having a core of magnetic material and an outer casing is inserted into the intestinal orifice. The casing is essentially cylindrical and is made of a material which is radially compressible, and inserted in the orifice, the magnetic material within the core thereof — which is preferably removable — in cooperation with the magnetic field from the permanent magnet locating the plug element within the orifice to establish an axial equilibrium position and hold the plug element in position closing the orifice.

14 Claims, 3 Drawing Figures

MAGNETICALLY OPERATED CLOSURE FOR AN INTESTINAL ORIFICE

BACKGROUND OF THE INVENTION

1. Field to which the invention relates

The present invention relates to a magnetically operated closure for an intestinal orifice.

2. The prior art

Closure devices for artificial or natural intestinal orifices have been proposed for example in the U.S. Pat. Nos. 3,565,073, 3,083,704, 2,243,529 and 3,952,726.

The U.S. Pat. No. 3,952,726 G. R. Hennig and K. G. Hennig, discloses a magnet arrangement which is implanted in the abdominal wall of the patient and surrounding the intestine in the vicinity of the orifice. A closure lid is provided which comprises magnetic material so that it is attracted by the implanted magnet arrangement to close the intestinal orifice. The implanted magnet arrangement can for example consist of an axially magnetised ring of a samarium-cobalt alloy, which is enveloped in a tissue-compatible material as for example polyoxymethylene (POM).

The closure device of the above mentioned type has been found highly satisfactory in practise; however, there are some applications for which it is not particularly suitable for example in the case of corpulent patients with a thick abdominal wall and in the case of an obliquely opening intestine. Furthermore the lid is often found to be troublesome when stooping and sitting.

THE INVENTION

It is an object to provide a magnetic closure device and closure plug, which are universally applicable also suitable for corpulent patients and for intestinal orifices of obliquely open intestine.

Briefly, a magnet which is shaped to at least in part surround the intestine, preferably an annular magnet, is implanted in the vicinity of the orifice to surround the intestine, the magnet being axially magnetized with respect to the intestine; a closure plug is provided which has a core of magnetic material and a casing which surrounds the core. The casing is of biologically compatible, compressible material and so shaped that the core surrounded by it can assume an axial equilibrium position with respect to the diametrically and axially directed magnetic interaction forces between the permanent magnet of the implantate and the core of the closure plug.

Even in the case of corpulent patients and obliquely opening intestine the magnetic closure device in accordance with the invention ensures a satisfactory and reliable closure. It causes practically no trouble and is pleasant to have after it has been fitted. Regardless of the depth of the intestinal orifice it can be used for closing artificial and natural intestinal orifices, in the case of which the intestine is provided adjacent to the orifice with an implanted magnetic arrangement.

A further advantage of the magnetic closure plug in accordance with the invention resides in that a pressure loading of the tissue and the skin, against which the casing of the magnetic closing plug makes sealing engagement is relatively small and very even so that there is practically no danger of necrosis. The secure seating and comfort are not impaired when the patient stoops and assumes a sitting pose.

Figure 1:
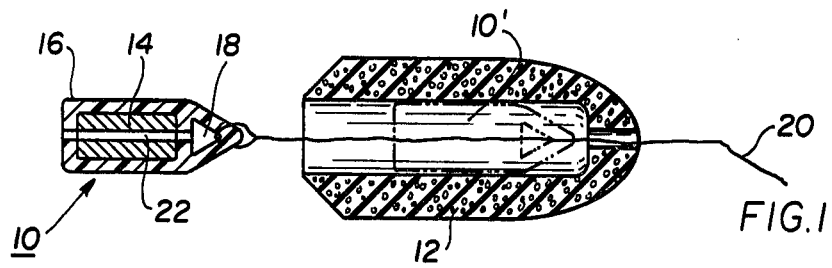
FIG. 1 shows an exploded section of view of a magnetic closure plug in accordance with a first embodiment of the invention.

The magnetic closure plug represented in FIG. 1 consists of a re-usable interior part 10 and an envelope or a casing 12 which is only to be used once. The interior part comprises a rod-shaped permanent magnet 14, which is longitudinally magnetised and is provided with an envelope 16 of a biologically compatible and resistant plastics as for example polymethylmetacrylate (PMMA). The plastics envelope 16 has an eye 18 at the front, with which a thread 20 is connected and with the thread 20 the interior part can be drawn into the casing 12 and the whole closure plug can be removed out of the intestinal orifice if required.

Figure 2:
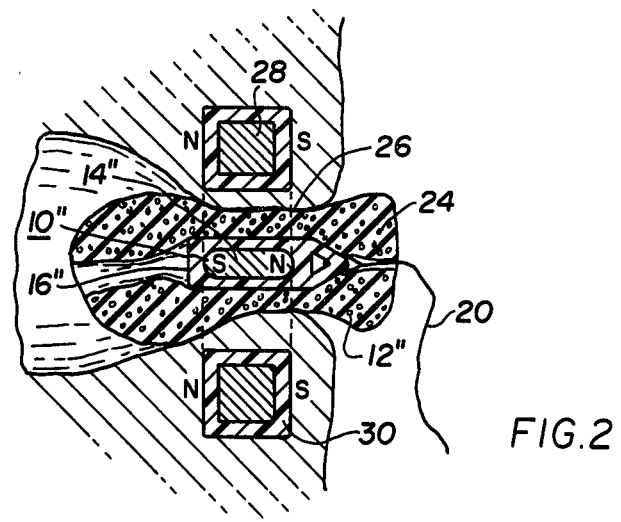
FIG. 2 shows a section representation of an artificial intestinal orifice, which is provided with a magnetic closure device in accordance with the invention which has a magnetic closing plug along the lines of that shown in FIG. 1.

The casing 12 consists of a material which at least in use is elastic, as for example foam material and before use is at least approximately cylindrical. In use it is pressed together in its centre by the intestinal orifice and accordingly has generally the shape of a hour glass (FIG. 2). The ends, which are made thicker than the centre part, and the magnetic force serve to hold the closure plug reliably in the intestinal orifice, where it bears and seals against the mucosa of the colon.

The permanent magnet 14 and the envelope 16 surrounding it can have an axial passage 22, through which gases can escape. Escape of gases is also possible if the casing consists of an open-pored foam material.

In the case of a magnetic closure plug ready for use of the type shown in FIG. 1 the interior part 10 is approximately in the centre of the casing, as is represented at 10' in broken lines.

The magnetic closure plug in accordance with FIG. 2 is the same in principle as that in accordance with FIG. 1 with the exception that the permanent magnet 14" in FIG. 2 and the casing 16" surrounding it do not have any hole. Furthermore the casing 12" has an odor absorbing or filter material 24 as for example activated carbon, for example in the form of a finely particulated powder.

The interior part, denoted in FIG. 2 by reference 10", of the magnetic closure plug is radially centered in the intestinal orifice 26 by the elastic casing 12". In the vicinity of the intestinal orifice the intestine is surrounded by an implanted annular permanent magnet 28, which, as has been previously proposed, is surrounded with an envelope 30 of tissue-compatible material as for example PMMA. The permanent magnet is axially magnetised, as is represented by the pole designations "N" and "S". The rod-shaped permanent magnet 14" of the closure plug, which is axially magnetised in the manner represented and is arranged in the manner shown, is held by the magnetic interacting forces axially in the centre of the annular permanent magnet 28, while the elastic forces, exerted by the casing 10 and/or the tissue surrounding it of the intestine, of the permanent magnet 14" of the closure plug tend to hold it in a radially centered position and to prevent it being tilted into a skew position. The magnetic forces of interaction therefore tend to hold the permanent magnet of the closure plug in a neutral, stable axial position of equilibrium and every movement out of its equilibrium position ("normal position") is opposed by the magnetic forces. Owing to this and the centering action of the casing, which is generally thickened or broadened out on both sides of the part of the intestine surrounded by the implantate, it is possible to ensure a firm seat of the magnetic closure plug.

Figure 3:
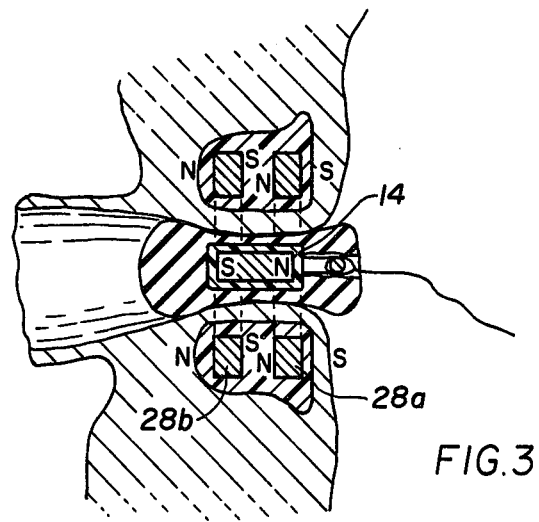
FIG. 3 shows diagrammatically an artificial intestinal orifice with a magnetic closure device in accordance with a further embodiment of the invention.

FIG. 3 shows a magnetic closure device which differs from that shown in FIG. 2 in that the implantate comprises two annular permanent magnets 28a and 28b, which are axially magnetised in the same direction and have a distance between them. The implantate can comprise two parts, which can be bonded firmly together so that it can be subsequently implanted without having to cut the intestine. As regards these features attention is called to the patent application by co-inventor Hennig, Ser. No. 803,240, June 3, 1977, corresponding to the published German Disclosure Document No. 26 25 234, December, 1977.

The closures plugs explained with reference to FIGS. 1 and 2 can be modified by using permanent magnets of a different shape, for example of a spherical shape or alternatively in lieu of a permanently magnetic material use can be made of a magnetic material with a high permeability and a low coercive force. The magnetic forces fixing the closure plug are then, however, somewhat smaller than is the case with the use of permanently magnetic material.

We claim:

1. In combination with a magnetically secured closure for the orifice of an intestine, having
    an implantate including
       a permanent magnet shaped to at least in part surround the intestine for implantation in the vicinity of the orifice and being, with respect to the intestine—axially magnetized;
    a closure plug comprising
       a core of magnetic material and
       a casing, surrounding the core, of a biologically compatible, compressible material, the casing being so shaped that the core surrounded by it can assume an axial equilibrium position with respect to the diametrically and axially directed magnetic interaction forces between the permanent magnet of the implantate, and the core of the closure plug.

2. A closure plug in accordance with claim 1, wherein the casing consists of a material which, when the closure plug is inserted into the intestine in the vicinity of the orifice, can be compressed radially; and which is separable from the core.

3. A closure plug in accordance with claim 2, wherein the material of the casing is an elastomer.

4. A closure plug in accordance with claim 2, wherein the casing in the unused condition is substantially cylindrical in shape and consists of an elastic material.

5. A closure plug in accordance with claim 2, wherein the casing consists of an elastic foam material.

6. A closure plug in accordance with claim 1, wherein the plug is formed with a passage through which gases can escape from the intestine.

7. A closure plug in accordance with claim 1, wherein the casing consists of a gas permeable material.

8. A closure plug in accordance with claim 1, wherein the core comprises an axially magnetized rod magnet, which is surrounded by the envelope of biologically compatible material.

9. A closure plug in accordance with claim 1, wherein the plug is formed with an eye for attachment of a thread thereto.

10. A closure device for an intestinal orifice, comprising an annular implantate, which includes at least one axially magnetized permanent magnet shaped for implantation to surround a zone of the intestine adjacent to its orifice;
    and a closure plug which includes a body of magnetic material and a casing surrounding it with a radially peripheral sealing surface, the plug being essentially cylindrical and shaped such that when the closure plug is inserted into the intestinal orifice its casing tends to center the body radially in the intestine; and wherein the magnetization of the magnetic system formed by the permanent magnet of the implantate and the body of magnetic material holds said plug in an axial normal position in the body and forming an axial equilibrium position with respect to magnetic forces of interaction between the implantate and the body
    whereby, upon movement of the plug out of this equilibrium position, magnetic forces are produced which tend to draw the body back into the equilibrium position.

11. A closure device in accordance with claim 10, wherein the body is an axially magnetized rod magnet.

12. A closure device in accordance with claim 1, wherein the implantate comprises an axially magnetized annular permanent magnet.

13. A closure device in accordance with claim 10 wherein the implantate comprises at least two annular permanent magnets, which are arranged with an axial spacing between them and are oppositely axially magnetized.

14. A closure device in accordance with claim 10, wherein the casing consists of a biologically compatible, elastically compressible material to effect elastic sealing engagement with the intestine adjacent its orifice.

* * * * *